United States Patent [19]
Nonomura

[11] Patent Number: 4,680,314
[45] Date of Patent: Jul. 14, 1987

[54] PROCESS FOR PRODUCING A NATURALLY-DERIVED CAROTENE/OIL COMPOSITION BY DIRECT EXTRACTION FROM ALGAE

[75] Inventor: Arthur M. Nonomura, Del Mar, Calif.

[73] Assignee: Microbio Resources, Inc., San Diego, Calif.

[21] Appl. No.: 771,402

[22] Filed: Aug. 30, 1985

[51] Int. Cl.[4] .................... A61K 31/07; A61K 31/355
[52] U.S. Cl. ..................................... 514/725; 514/458
[58] Field of Search ...................... 424/195.1; 514/725, 514/763, 458

[56] References Cited

U.S. PATENT DOCUMENTS 4,435,427  3/1984  Hoppe et al. ...................... 514/763

OTHER PUBLICATIONS

Merck Index, 9th ed., 1976, Nos. 1852–1855, pp. 236–237.
T. W. Goodwin, "Chemistry and Biochemistry of Plant Pigments", 2nd ed., vol. 1, Academic Press, pp. 161–163, 1976.
T. W. Goodwin, "Chemistry and Biochemistry of Plant Pigments", 2nd ed., vol. 2, Academic Press, pp. 69–75, 1976.
D. Perrin et al, "Purification of Lab. Chemicals", Pergamon Press, pp. 159–160, 1980.
E. Stahl, "Thin–Layer Chromatography", 2nd ed., pp. 266–273, 1969.
D. Swern, Bailey's Industrial Oil and Fat Products, vol. 1, 4th ed., Wiley Pub., p. 69.

Primary Examiner—Johnnie R. Brown
Assistant Examiner—John W. Rollins, Jr.
Attorney, Agent, or Firm—Becker & McClain

[57] ABSTRACT

A process is described for the formation of a naturally derived composition comprising carotenes, particularly beta-carotene, in oil. The process involves the direct oil extraction of the carotene from algae. The algae are initially harvested as a water slurry and concentrated, as by flocculation, in the slurry. The concentrated portion of the slurry is then mixed with oil and homogenized to form an oil emulsion. Direct contact of the oil and algae results in a high degree of extraction of the carotene from the algae by the oil. The water/oil emulsion is broken and the oil phase containing the carotene separated as by centrifugation and recovered. The resulting carotene/oil composition is useful as a precursor in formation of Vitamin A in human nutrition. The carotene itself may also have some use as a preventative material for certain types of cancers or in supplementation of poultry and livestock feed.

20 Claims, 1 Drawing Figure

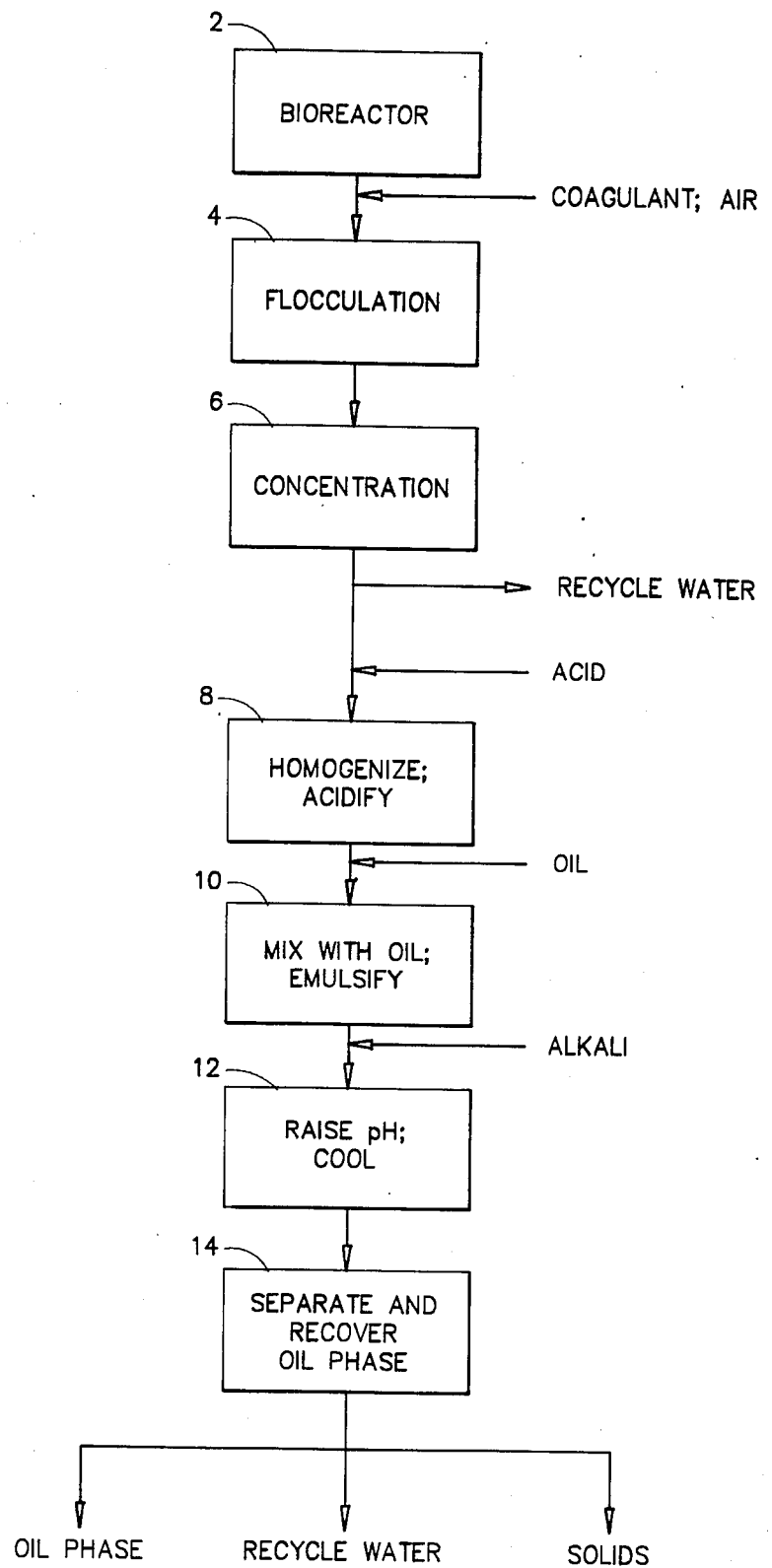

PROCESS FOR PRODUCING A NATURALLY-DERIVED CAROTENE/OIL COMPOSITION BY DIRECT EXTRACTION FROM ALGAE

FIELD OF THE INVENTION

This invention relates to processes for production of carotene/oil compositions, particularly those containing beta-carotene.

BACKGROUND OF THE INVENTION

Retinol (Vitamin A) is known to be necessary to the biochemistry of human vision. Through a series of reactions, the retinol is converted through retinal isomers to rhodopsin ("visual purple"). Irradiation of the rhodopsin with visible light in turn causes a series of isomerization reactions through the retinal isomers to opsin resulting in excitation of the retinal rod cells and generation of a visual nerve impulse. A deficiency of Vitamin A in the system leads to reduced visual sensitivity (especially night blindness) and in extreme cases (e.g., keratomalacia or xerophthalmia) to complete blindness.

Vitamin A is also known to be necessary to the proper function of the epithelial tissues. Deficiency of Vitamin A in such cases results in disorders such as reduced resistance to infection through epithelial surfaces.

Increases of level of Vitamin A in the body may to some extent be obtained by administering doses of Vitamin A directly to an individual. However, there is a limited bodily tolerance to Vitamin A, and overdoses of Vitamin A can lead to toxic effects. Since the tolerance level varies widely among individuals, it is not generally advisable to administer substantial doses of Vitamin A except under carefully controlled circumstances.

It is well known that carotene is the precursor of Vitamin A. (There are several carotene isomers, including the alpha-, beta- and gamma- isomers. Of these the beta- isomer is the most active for Vitamin A activity and is also the most common. As used herein, the terms "carotene" or "the carotenes" will refer to mixtures of two or more of the isomers or to an individual isomer as appropriate to the context. If a particular isomer is of specific importance in a given context, it will be so identified.) The carotenes are oxidized by liver enzymes to produce Vitamin A. Significantly, however, the enzyme metabolism produces only the amount of Vitamin A that can be utilized by the body; it cannot produce an overdose of Vitamin A. Consequently, an individual can be administered doses of carotene in quantities large enough to produce optimum levels of Vitamin A in the body without the risk of a toxic Vitamin A reaction. Excess carotene which is administered is stored in fatty tissues and organs.

The carotenes, particularly beta-carotene, are present in many common foods, primarily the green and yellow vegetables such as tomatoes, citrus fruits, carrots, squash, turnips, broccoli and spinach. The concentration of carotene in these vegetables is relatively low, and a person must consume substantial quantites of the vegetables to have a high intake level of carotene. The normal diet of most people does not include such large quantities of these types of vegetables, so there has developed a commercial market for concentrated carotene dietary supplements, particularly those in which the carotene is beta-cartoene because of its high Vitamin A activity. These supplements normally have been produced by extraction of carotene from vegetables such as carrots by use of petrochemical solvents. The resulting carotene, usually in crystalline form, can be expected to be associated with at least residual quantities of such solvents. This is particularly true when the carotene is administered in a dosage form in which it is dispersed in a petrochemical or other "synthetic" oil. The presence of such petrochemical residues in the carotene supplements, even in minute amounts, has caused apprehension among users of the supplements.

It is also known that certain algae, especially those in the classes Rhodophyta (red algae) and Chlorophyta (green algae), are good sources of carotene. The carotene content of species of the genus Dunaliella have been reported in U.S. Pat. Nos. 4,115,949 and 4,119,895 and in *Acta Chem. Scand.*, 23, 7, 2544–2545 (1979). Similar data for the genus Chlorococcum are disclosed in U.S. Pat. No. 2,949,700. In the past, however, extraction processes to produce the carotene from algae have involved the use of petrochemical solvents, which produces the same residual contamination problems discussed above for the vegetable extractions. In addition, many of the algal extraction processes have involved drying of the alga, which has been found to reduce the yield of carotene which may be recovered from the alga. Typical of such extraction processes are those described in the aforesaid U.S. Pat. Nos. 4,155,949 and 4,199,895, which use solvents such as hexane and cyclohexane.

In addition to the use of carotene as a precursor for Vitamin A, there have recently been reports in the literature that suggest that carotene is itself useful in the prevention of certain types of cancers which are believed to be promoted by oxidizing free radicals. It is postulated that carotene, which has an affinity for such free radicals, may serve to reduce the free radical level in the body, thereby reducing the occurrence of free radical initiation of malignancies. There are studies currently underway which are expected to provide more information regarding the effects of carotene on such cancers.

The carotenes can also be used in supplementation of poultry and livestock feeds.

It would therefore be of benefit to have a process available which would yield commercial quantities of carotene in a form which would be safe and therapeutically useful for humans, and which would not result in petrochemical contamination of the carotene. It would also be advantageous for such a process to be capable of extracting and recovering virtually all of the available carotene from algae without the significant losses encountered in the prior art processes which involve thorough drying of the algae.

BRIEF SUMMARY OF THE INVENTION

The invention herein is a process for the production of a naturally-derived composition comprising carotene dissolved in edible oil. The process comprises:
  a. providing a slurry of carotene-containing algae suspended in water;
  b. concentrating the algae at or near the surface of the water and thereafter removing a portion of the water to form a wet algal concentrate;
  c. adding oil to the wet algal concentrate and homogenizing the mixture to form an oil/water emulsion and allowing said emulsion to exist for a time sufficient to extract the carotene from the algae into the oil by direct contact of the oil with the algae; and thereafter separating the oil phase containing the carotene from the water and recovering the naturally-derived composition comprising the oil containing the carotene dissolved therein.

In preferred embodiments the carotene isomers, particularly the beta-carotene isomer, are individually recovered.

The algal raw materials for this process will be from the classes Chlorophyta and Rhodophyta, of which the preferred genera are Chlorococcus and Dunaliella, particularly the Dunaliella genus.

In a preferred embodiment, the concentration of step (b) is attained by flocculating the slurry, floating the algae, decanting the excess water to form a wet algal concentrate and thereafter acidifying the concentrate to decomplex the flocculant from the algae.

In another embodiment, the acid-containing slurry after decomplexing is treated with an alkaline material to raise the pH to a substantially neutral value. The slurry may also be cooled at that time. Both of these measures simplify the subsequent separation and recovery steps.

The preferred oil to be used is a vegetable oil such as corn oil, safflower oil or the like. Edible oils from animal sources such as fish may also be used.

For the purpose of this invention the term "naturally derived" means that throughout the present process none of the steps involve the use of petrochemical solvents or reactants. Additionally, the term also encompasses the requirement that the algae and oil have not previously been grown or produced with mineral or petrochemical materials. Beta-carotene and the various vegetable oils are of course naturally occurring materials, but the term "natural" has unfortunately frequently been misused in the commercial vitamin supplement field in the past few years. Products are labeled "natural" although they have been produced with, treated by or combined with synthetic or petrochemical chemicals such as solvents. Thus, while the principal active ingredient may be a naturally occurring material, the entire formulation used as the vitamin supplement contains significant and often predominant quantities of materials which are frequently not part of the human diet. Consequently, the term "naturally derived" is used herein to provide an appropriately precise definition.

BRIEF DESCRIPTION OF THE DRAWING

The single FIGURE of the drawing is a flow diagram indicating schematically the various steps which may be used in this process.

DETAILED DESCRIPTION OF THE INVENTION

The present invention provides for the direct extraction of carotene from algal sources by contacting naturally derived oils under controlled conditions directly with the algae. This direct extraction of the carotene into the oil provides for much better yields of carotene than heretofore possible with many processes; it is common in this process for yields of 80–95% or better to be obtained.

The alga (or in the case of mixed species, the algae) which is used in the present invention may be any in which carotene is present in large quantities. It is known that carotene exists in many genera of algae and that in certain of these genera advanced cultivation techniques can significantly increase the amount of carotene in each algal cell. Typically, the alga is raised in natural ponds or manmade bioreactors and by controlled feeding techniques the alga is caused to increase carotene content. The culture medium is salt or fresh water, depending on the alga used. Fresh water made saline by addition of salt or seawater may be used for salt water media. It is preferred to use fresh water made saline by addition of salt as the culture medium, since that allows one in many cases to produce and maintain unialgal cultures. When the carotene reaches the desired level, the alga is harvested from the bioreactors. As noted, in prior art processes the alga was then subjected to various steps of such treatments as drying, milling and solvent extraction followed by crystallization to produce carotene. Such processes resulted in loss of carotene. In addition, the various solvent extraction processes and drying steps caused the carotene to be degraded and the ultimate yield to be rather low.

The preferred algae for the present process are the genera Chlorococcus and Dunaliella, of which the Dunaliella genus is most preferred.

Reference to FIG. 1 will illustrate the process of the invention, as exemplified with a single algal species. The alga is initially cultiviated in bioreactor 2 which, as noted, is a natural pond or artificial bioreactor (both collectively referred to herein as "bioreactor" for brevity). The alga is harvested from the bioreactor by pumping out the water slurry containing the dispersed alga. If desired, the bioreactor water may be held in tanks to allow any foreign objects to settle. Commonly the water may also be passed through screens which are sufficiently coarse to allow the alga to pass freely through but which will remove larger unwanted objects.

The slurry is then concentrated in algal content to allow removal of unneccessary water, so that the excess water does not need to be handled later in the process. Such concentration may be by a variety of known concentration techniques, such as centrifugation, evaporation, etc. Preferred, however, is flocculation, usually on a continuous basis, in flocculating zone 4. To the water containing the alga is added a coagulating agent such as alum or ferric chloride and the coagulant is mixed thoroughly into the water. The coagulant coats the individual algal cells and causes them to flocculate so that they can be floated to concentrate at or near the surface of the water. The techniques of flocculation and flotation are well known, and any convenient method (including any known enhancement procedures) may be used. The flocculation may be performed in any conventional mixing apparatus, as illustrated in flocculation zone 4. The system commonly operates continuously with thoroughly flocculated material being withdrawn from the outlet side of the zone as new material is being added for mixing at the inlet.

The flocculated algal slurry is concentrated in concentration tank 6 by floating the flocculated alga to the surface of the water to be skimmed off along with a small portion of the water, forming a wet algal concentrate. The remaining water from which virtually all of the alga are thus removed (usually 95% or better) is decanted and is recycled back to the bioreactors.

The pH of the concentrate is then adjusted, usually by acid treatment, to remove the flocculant. In order to break many flocculations, the acid must be one which will produce a pH of approximately 2.5 or lower. Preferred will be the organic acids, of which the most preferred is citric acid. The strong inorganic acids such as hydrochloric acid or phosphoric acid may also be used. After addition of the acid the concentrate is thoroughly mixed or homogenized as in step 8. The flocculation is decomplexed and the cells are dispersed evenly throughout the water. Typically the system is also heated to a temperature on the order of 80° C. to rapidly remove the flocculant from the cells. The system is also mechanically homogenized to cause the cells to be at least partially liquefied. This latter operation is particularly important when the algal species used is one with a cell wall. The time required for thi operation is not more than two hours for completion of homogenization in typical commercial vessels; times will be adjusted accordingly for particular vessel volumes.

Following concentration of the slurry, and if desired at the same time as the acid decomplexing if flocculation is used in the concentration step, oil is added to the system in an amount calculated to result in a final oil product containing 0.5–7.5 weight percent carotene. A wide variety of edible oils may be used including both animal and vegetable oils, although the vegetable oils are much preferred. Typically the oils which may be used are corn oil, safflower oil, peanut oil and numerous others, including mixtures of oils. As the oil is mixed with the water slurry in Step 10, the homogenizer serves to form a water/oil emulsion. No extra emulsifier is used to support the emulsion. The extraction of the carotene from the algal cells into the oil occurs with or following the acid reaction removing the flocculant from the alga. The oil extraction is conducted at a temperature of 66°–100° C. and continues until the oil is thoroughly emulsified to droplets on the order of 10–100 μm. The carotene extraction is normally a minimum yield of 80% and usually 95% or better.

After the oil extraction is completed the oil/water emulsion is broken to recover the oil containing the carotene. A variety of means can be used to break the emulsion and for the separation, including centrifuging, gravitational settling and vacuum filtration. Centrifuging is the preferred method since gravitational settling is less efficient and filtration results in significant oil absorption by the filter medium.

It would be most efficient if the separation could be conducted without significantly changing the pH and temperature of the homogenized slurry. It is intended that such a step is considered part of the present invention. As a practical matter, however, it has been found that corrosion of the separation equipment can be severe when the highly acid hot slurry is used. Therefore, in order to prolong the service life of the separation equipment, it is desirable to raise the pH of the slurry to an essentially neutral value on the order of pH 7 and to cool the slurry to a temperature at which chloride corrosion from the salt water is minimized. This is shown at 12 in FIG. 1 and is normally accomplished by adding sodium hydroxide or a similar alkali to the system. Reaction of the acid and the alkali results in an exothermic reaction so additional cooling is usually required.

Once the slurry has been cooled and neutralized, it is separated at step 14 to recover the carotene containing oil. A continuous triple centrifuge has been found quite useful, which separates the incoming slurry into three components: the carotene containing oil (the light phase); a heavy liquid phase composed of the salt water, residual alkali, acid and flocculant and a solids phase consisting of the algal residue mixed with a small amount of water. Proper operation of the centrifuge has been found to provide clean separation of these phases with only minimal entrainment of any water in the oil phase. Such entrained water is easily removed by allowing the oil to settle and decanting the small amounts of water which occur. The collected oil phase therefore contains virtually all of the carotene and no significant amounts of any of the other processing materials.

The direct oil process extracts not only the carotenes but also the chlorophylls in the algae. Each of the carotene isomers and/or the chlorophyll products may be separated and individually recovered if desired. Alternatively they may be used as the mixed isomers (with or without the chlorophyll products); since all have some Vitamin A activity, the extracted material is especially beneficial for dietary supplement use.

The collected oil phase containing the carotene is subsequently converted to dosage form, usually by encapsulating the oil in gelatin. It is desirable to include a small amount of mixed tocopherols (Vitamin E) as a stabilizer.

In a specific example of this process, carotene was extracted from *Dunaliella salina*. The *D. salina* was harvested from bioreactors and flocculated using alum. The flocculated slurry was skimmed and approximately 50% of the water was decanted for recycle. Thereafter addition of dry granular citric acid at a ratio of about 5–10% acid in the slurry was used to decomplex the flocculated alga. Corn oil containing 0.3% mixed tocopherols was added in a quantity sufficient to produce a desired oil concentrate of about 2% carotene and the entire oil/water slurry was emulsified by the homogenizer at a temperature of 80° C. for a period of approximately 45 minutes and at an acidity level on the order of pH 2. Thereafter the system was neutralized using sodium hydroxide and the temperature was reduced to 40° C., following which it was centrifuged to recover the desired oil/beta-carotene product. The oil composition was found to have approxmately 1.9% by weight carotene and less than 0.2 weight percent each of alpha-carotene and other carotenoids. The solution was diluted with additional oil to produce a final carotene concentration of 1.4% by weight.

It will be evident that there are other embodiments not specifically described above which are clearly within the scope and spirit of the invention. Therefore, this description is to be taken as exemplary only and the scope of the invention is to be determined solely by the appended claims.

I claim:

1. A process for the production of a naturally-derived composition consisting essentially of carotene dissolved in edible oil, which comprises:
    a. providing a slurry of carotene-containing algae suspended in water;
    b. concentrating the algae at or near the surface of the water and thereafter removing a portion of the water to form a wet algal concentrate;
    c. adding oil to the wet algal concentrate and homogenizing the mixture to form an oil/water emulsion and allowing said emulsion to exist for a time and at a temperature sufficient to extract the carotene from the algae into the oil by direct contact of the oil with the algae; and thereafter separating the oil phase containing the carotene from the water and recovering the naturally-derived composition consisting essentially of the oil containing carotene dissolved therein.

2. A process as in claim 1 wherein the recovered carotene is separated to yield beta-carotene.

3. A process as in claim 2 wherein said alga is selected from the classes Rhodophyta and Chlorophyta.

4. A process as in claim 3 wherein said alga is selected from the Chlorococcus and Dunaliella genera.

5. A process as in claim 4 wherein said alga is of the genus Dunaliella.

6. A process as in claim 5 wherein said alga is *Dunaliella salina*.

7. A process as in claim 1 wherein the recovered carotene is separated to yield alpha-carotene.

8. A process as in claim 1 wherein the recovered carotene is separated to yield gamma-carotene.

9. A process as in claim 1 wherein said concentration of Step (b) is attained by flocculating the slurry and floating the algae at or near the surface of the water, decanting the excess water to form the wet algal concentrate and thereafter adjusting the pH of the concentrate to decomplex the flocculant from the algae.

10. A process as in claim 9 wherein said pH adjustment comprise acidification.

11. A process as in claim 10 wherein said acidification and decomplexing occurs with or following the homogenization and formation of said oil/water emulsion.

12. A process as in claim 1 wherein said separation of Step (c) is obtained by centrifugation.

13. A process as in claim 1 wherein said alga is selected from the classes Rhodophyta and Chlorophyta.

14. A process as in claim 13 wherein said alga is selected from the Chlorococcus and *Dunaliella genera*.

15. A process as in claim 14 wherein said alga is of the genus Dunaliella.

16. A process as in claim 15 wherein said alga is *Dunaliella salina*.

17. A process as in claim 1 wherein said edible oil is a vegetable or animal oil.

18. A process as in claim 17 wherein said edible oil is a vegetable oil.

19. A process as in claim 18 wherein said vegetable oil is corn oil, safflower oil, peanut oil, coconut oil or mixtures thereof.

20. A process as in claim 1 further comprising, prior to step (a), raising the algae in a culture medium of fresh water made saline by addition of salt, and from which said slurry is obtained.

* * * * *